(12) United States Patent
Redoules et al.

(10) Patent No.: US 7,084,172 B2
(45) Date of Patent: Aug. 1, 2006

(54) BIOPRECURSORS FOR PERCUTANEOUS APPLICATION

(75) Inventors: Daniel Redoules, Toulouse (FR); Pascal Bordat, Mervilla (FR); Jean-Jacques Perie, Castanet (FR)

(73) Assignees: Pierre Fabre Dermo-Cosmetique, Boulogne (FR); Universite Paul Sabatier Toulouse, Toulouse (FR)

( * ) Notice: Subject to any disclaimer, the term of this patent is extended or adjusted under 35 U.S.C. 154(b) by 39 days.

(21) Appl. No.: 10/489,736

(22) PCT Filed: Sep. 16, 2002

(86) PCT No.: PCT/FR02/03148

§ 371 (c)(1),
(2), (4) Date: Mar. 16, 2004

(87) PCT Pub. No.: WO03/024952

PCT Pub. Date: Mar. 27, 2003

(65) Prior Publication Data

US 2004/0236098 A1   Nov. 25, 2004

(30) Foreign Application Priority Data

Sep. 17, 2001   (FR) .................. 01 11982

(51) Int. Cl.
*A61K 31/355* (2006.01)
*C07D 311/72* (2006.01)

(52) U.S. Cl. ...................... 514/458; 549/410

(58) Field of Classification Search ............... 549/410; 514/458

See application file for complete search history.

(56) References Cited

U.S. PATENT DOCUMENTS 2,407,726 A * 9/1946 Smith et al. ................ 549/410
2,680,749 A * 6/1954 Cawley et al. .............. 549/410
6,180,669 B1 * 1/2001 Tamarkin .................... 514/548

FOREIGN PATENT DOCUMENTS

GB    2285805 A  * 7/1995
GB    2285805 A1 * 7/1995
JP    03206021 A2 * 9/1991
WO    WO 00/58325   10/2000
WO    WO00/61189    10/2000

OTHER PUBLICATIONS

Basinski, D. et al. Journal of Biological Chemistry 1947, 167, 339-343.*
Rosenkrantz, H. Journal of Biological Chemistry 1948, 173, 439-447.*
Harris, P. L. et al. Journal of Biological Chemistry 1949, 180, 611-614.*
Miller, W. H. et al. Annals of the New York Academy of Sciences 1949, 52, 167-79.*
Duval, C. et al, "Scavenger Effect of Vitamin E and Derivatives on Free Radicals Generated by Photoirradiated Pheomelanin," Journal of Pharmaceutical Sciences, vol. 84, No. 1, Jan. 1995, pp. 107-110.
Chemical Abstracts, vol. 109, No. 30, 1988, Abstract 73692 Araskawa S., et al. (Aug. 1987) (AJP) "Preparation of tocopherol/tocofriend-L-ascorbic acid-6-dicarbcyylete esters as pharmaceuticals".

* cited by examiner

*Primary Examiner*—Kamal A. Saeed
*Assistant Examiner*—Jason M. Nolan
(74) *Attorney, Agent, or Firm*—Steptoe & Johnson LLP

(57) ABSTRACT

The invention concerns a bioprecursor of formula (I), wherein $A_1$ and $A_2$ represent independently of each other a radical derived from a molecule capable of being used in dermatology or in cosmetology; X and Y represent independently of each other a hydrogen atom, a hydroxy group or a $C_1$–$C_{20}$ alkyl group; and n represents an integer between 0 and 10

(I)

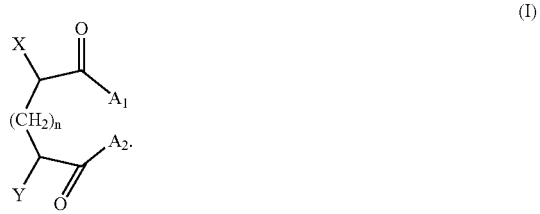

10 Claims, No Drawings

BIOPRECURSORS FOR PERCUTANEOUS APPLICATION

The present invention relates to a cosmetic or pharmaceutical composition for cutaneous application, containing a compound capable of releasing two active molecules (in particular vitamins) via the action of an esterase activity contained in the skin, the spacer possibly introducing an additional effect (for example moisturizing effect of hydroxy acid).

It has previously been shown, using two sources of cutaneous enzymes, that this enzyme is indeed capable of recognizing and hydrolyzing succinic esters, thus allowing slow release of the active substance, without an accumulation effect (M. P. Mora et al., Chem. Phys. Lipids (1999), 101, 255–265, J. R. Trevithick et al., Biochem. Mol. Biol. Int. (1999), 47, 509–511).

The bioprecursor strategy has previously been used for the release of active agents, especially in the following cases:

release of retinol from its ester with palmitic acid.

Many compounds are used in dermatology, among which the following will be selected:

moisturizers, or more specifically agents for controlling skin perspiration, such as saccharides (glucose, sorbitol or hyaluronic acid), but also glycerol and α-hydroxy acids, or even ceramides of plant origin, which moisturize via their polar portion. Among the hydroxy acids, L-ascorbic acid is an agent of choice, since it combines this primary property with other effects: an antioxidant effect and also the ability to stimulate collagen synthesis (and thus the synthesis of elastic fibres) via a specific increase in the level of mRNA coding for the three pro-α chains. Furthermore, ascorbic acid activates the enzyme that effects the formation of collagen from procollagen (S. R. Pinel et al., Arch. Dermatol. (1987), 123, 1684–1687);

antioxidants: it is known that they are essential to avoid the degradation of lipids via the action of radicals and also other damage to biomolecules of the skin surface, this damage resulting in the formation of wrinkles. Among the main free-radical scavengers found are tocopherols, flavonoids, ascorbic acid and metal-chelating agents, which blockade the oxidation reactions catalyzed by said metals;

agents for controlling differentiation: the most important is vitamin A or retinol, since a deficiency is reflected by hyperkeratinization and also atrophy of the sebaceous glands and the sweat glands. Retinol is not used in its native form, but after two enzymatic oxidations, the first reversible, which converts it into retinal, and the second irreversible, converting it into retinoic acid, which is the active form that acts on the nuclear receptors. It is stored in the form of linoleic and palmitic esters. A supply may be provided in the form of esters or in the form of retinol linked to a vector. It is known that the action of retinoic acid is manifold: activator of cell metabolism and control of keratinization, antioxidant and thus prevention of the formation of wrinkles, action, on the dermis, on the metabolism of fibroblasts via two effects: inhibition of the collagen-degrading enzymes (collagenases) and stimulation of glucosaminoglycans which increase the content of collagen and thus increase the elasticity of the skin;

vitamin D, which, besides its action on phosphocalcic metabolism, exerts via its biologically active form, calcitriol, effects on cell proliferation and differentiation. Specifically, incubation of human keratinocytes with calcitriol results in a decrease in their proliferation and induction of their terminal differentiation (M. F. Holick et al., Arch. Dermatol. (1987), 123, 1677–1683). Calcitriol is also a powerful immunosuppressant, which inhibits lymphocyte activation and the production of immunoglobulins (M. Bagot et al., Br. J. Dermatol. (1994), 130, 424–431).

The direct topical use of these derivatives comes up against a certain number of difficulties, due to their lack of stability over time and to light, and secondary effects (prooxidizing and irritation effects) often resulting from local overconcentrations of the active molecules.

The value of improving the bioavailability of active agents conveyed in the form of a precursor in which they are associated, and thus of avoiding their harmful effects caused by accumulation, may thus be seen.

After investigating the expression by keratinocytes of lipase or cholesterol esterase activity, the inventors have identified lysosomial acid lipase (Human Lysosomial Acid Lipase or HLAL, Anderson R. A. et al., J. Biol. Chem., 266, 22479–84) and have shown, surprisingly, that this esterase is capable of cleaving certain precursors that are in the form of esterified active agents.

Consequently, the present invention relates to a bioprecursor of formula (I)

in which $A_1$ and $A_2$ represent, independently of each other, a radical derived from a molecule capable of being used in dermatology or cosmetology, and X and Y represent, independently of each other, a hydrogen atom, a hydroxyl group or a $(C_1–C_{20})$alkyl group; and n represents an integer between 0 and 10.

For the purpose of the present invention, the expression "compound capable of being used in dermatology or cosmetology" means, besides all of the agents defined in the above list, antibiotics, for instance retronidazole, erythromycin, tetracycline and clindamycin, antibacterial agents, nonsteroidal antiinflammatory agents and vitamins.

In one particular embodiment of the invention, the molecule capable of being used in dermatology or cosmetology has antiinflammatory, antibacterial, antibiotic or vitamin activity.

In another particular embodiment of the invention, $A_1$ and $A_2$ represent, independently of each other, an ascorbyl, cholecalciferyl, retinyl or tocopheryl radical.

In one particularly advantageous embodiment of the invention, $A_1$ represents a tocopheryl radical and $A_2$ represents a radical chosen from the group comprising retinyl, cholecalciferyl and ascorbyl radicals.

In an even more advantageous embodiment according to the invention, the compound of formula (I) is chosen from the group consisting of tocopheryl retinyl succinate, tocopheryl cholecalciferyl succinate and tocopheryl ascorbyl succinate.

The present invention also covers pharmaceutical or cosmetic compositions for topical use containing at least one bioprecursor of formula (I) combined with a vehicle that is suitable for percutaneous administration.

In accordance with the present invention, when said composition is applied to the skin, the complex undergoes an enzymatic hydrolysis of esterase type leading to the release of the active principle, said active principle being released in a delayed manner, without any accumulation in the various layers of the skin.

The compositions according to the invention contain from 0.001% to 10% by weight and preferably 0.01% to 0.1% by weight of bioprecursors relative to the total weight of the composition.

They may be in the form of an oil-in-water (O/W) or water-in-oil (W/O) emulsion. They may also be in the form of spherules, for instance liposomes, nanocapsules or nanospheres.

When the compositions are emulsions, the proportion of the fatty phase ranges from 5% to 80% by weight and preferably from 5% to 50% by weight relative to the total weight of the composition. The oils, emulsifiers and coemulsifiers used in these compositions, in emulsion form, are chosen from those conventionally used in cosmetics. The emulsifier and the coemulsifier are present in the compositions in a proportion ranging from 0.3% to 10% by weight relative to the total weight of the composition.

The compositions according to the invention may also contain acceptable cosmetic or dermatological additives. These additives may be, in particular, antioxidants, other bioprecursors of these antioxidants, for instance δ-tocopheryl glucopyranoside, surfactants, fatty substances, moisturizers, preserving agents, fragrances, gelling agents, chelating agents, pigments, for instance titanium oxide, screening agents and free vitamins.

The bioprecursors of formula (I) are prepared via techniques known to those skilled in the art.

In one particularly advantageous embodiment of the process, a compound of formula (II)

$$A_1\text{-H} \quad (II)$$

in which $A_1$ is as defined above, is reacted with a compound of formula (III)

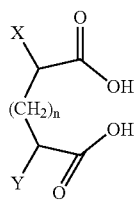

(III)

in which X and Y are as defined above, in a mixture containing a solvent, for instance anhydrous dichloromethane, triethylamine, II, III, dicyclohexylcarbodiimide (DCC) and dimethylaminopyridine (DMAP), to give a compound of formula (IV)

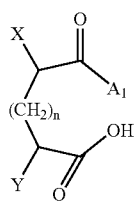

(IV)

which compound is reacted under the same conditions as above with a compound of formula (V)

$$A_2\text{-H} \quad (V)$$

to give the compound of formula (I).

In another advantageous embodiment of the process according to the invention, the compound of formula (II) is reacted with an activated form of the compound of formula (III), for example succinic anhydride.

The advantages of this bioprecursor strategy are the following:

stabilization of the active agent by means of neutralizing the most reactive hydroxyl function (vitamins D, E or A). Due to the size of the esterase activity in the live layers of the epidermis and to its virtual absence in the horny layer (U. K. Jain et al., Proceed. Intern. Symp. Control. Rel. Bioact. Mater. (1995), 22, 702–703), the precursors that represent the stabilized form of the active principles are preserved throughout the slow migration through the horny layer, which corresponds to the part that is the most exposed to oxidative stress (UV and ozone) (G. Valacchi et al., FEBS Letters (2000), 446, 165–168);

release at a controlled rate (taking into account the very precise regulation of the skin physiology) and reservoir effect.

Furthermore, targeted release from the stratum granulosum at the level of the plasma membranes of the keratinocytes is obtained (M. P. Mora et al., Chem. Phys. Lipids (1999), 101, 255–265), i.e. immediately at the start of the live part of the epidermis.

The precursor, after migration into the first layers of the live epidermis, i.e. into the stratum granulosum, is recognized as a pseudosubstrate via the involved esterase activity, which is responsible for the hydrolysis of the two ester functions. Two conjugate, additive or even synergistic, effects are thus obtained using a single formulation, this formulation facilitating migration.

Thus, the tocopherol-ascorbic acid combination is particularly advantageous, since the ascorbic acid regenerates the tocopherol after its oxidation, thus increasing its antioxidant efficacy.

The structure of the precursors according to the invention ensures good stability throughout the passage through the layer and release of the active agents into the live layers of the epidermis, with kinetics that ensure effective cleavage and an effect with remanence over time.

The penetration through the skin is associated with the Kd of the compounds (Agache P. et al., Ed. Tech. Encycl. Med. Chir. (1995), 12-235-C-30, 1–10); however, the structure of the precursors according to the invention also makes it possible to modulate the penetration of the pseudo-substrate active agents by virtue of the presence of X and Y which represent either hydroxyl groups, and are thus hydrophilic, or $(C_1$–$C_{20})$alkyl groups, and are thus lipophilic, which make it possible to obtain an amphiphilic compound capable of penetrating in an appreciable amount via passive diffusion.

The examples that follow illustrate the invention without, however, limiting it.

EXAMPLE 1

O-(4-Oxo-4-{[2,5,7,8-tetramethyl-2-(4,8,12-trimethyltridecyl)-3,4-dihydro-2H-chromen-6-yl]oxy}butanoyl)retinol or tocopheryl retinyl succinate (CV-105)

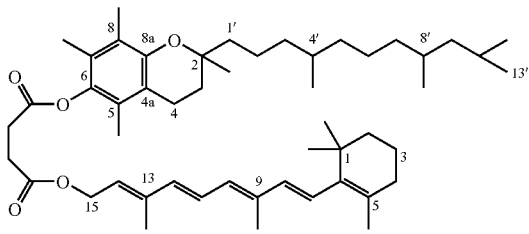

1.1. Methyl 2,5,7,8-tetramethyl-2-(4,8,12-trimethyltridecyl)-3,4-dihydro-2H-chromen-6-yl succinate (CV-104)

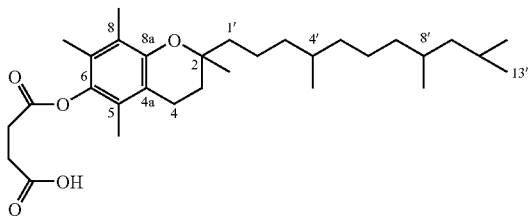

Two synthetic methods were developed, starting either with succinic anhydride or with succinic acid.

According to the first method, α-tocopherol or vitamin E (2.15 g, 5 mmol) and succinic anhydride (750 mg, 7.5 mmol, 1.5 eq) are dissolved in 20 ml of anhydrous dichloromethane ($CH_2Cl_2$). Dimethylaminopyridine (DMAP) (305 mg, 2.5 mmol, 0.5 eq) and anhydrous triethylamine (0.7 ml, 1 eq) are added thereto and the reaction is monitored by thin-layer chromatography (tlc) ($Et_2O$/petroleum ether (PE) 2:3 or ethyl acetate/PE 1:1). The reaction is generally complete after reacting overnight, and the mixture is thus filtered and then washed with aqueous 5% hydrochloric acid (HCl). The organic phase is dried over $MgSO_4$ and then evaporated to give a yellow oil (about 3 g) to be purified.

According to the second method, succinic acid, (590 mg, 5 mmol), dicyclohexylcarbodiimide (DCC) (1.03 g, 1 eq) and DMAP (61 mg, 0.5 mmol, 10%) are dissolved in 20 ml of anhydrous $CH_2Cl_2$ with ultrasonication for 10–15 minutes, after which a-tocopherol or vitamin E (2.15 g, 5 mmol, 1 eq) dissolved in 10 ml of anhydrous $CH_2Cl_2$ is added thereto. The reaction is monitored by tlc ($Et_2O$/PE 2:3 or EtOAc/PE 1:1). The mixture is thus filtered and then washed with aqueous 5% HCl and the organic phase is dried over $MgSO_4$ and then evaporated to give a yellow oil to be purified.

In both cases, the product is purified by flash chromatography (2.5 cm×16 cm column, eluent $Et_2O$/PE 2:3, 10–15 ml fractions). The deposition of the pasty oil may take place as a solid deposit or in $CH_2Cl_2$. The first method gives 2.26 g of pure CV-104, i.e. 85% yield, and the second method gives 1.95 g, i.e. 73% yield of a pale yellow oil that hardens at −20° C. and can give a white powder.

Rf ($Et_2O$/PE 2:3): 0.39. $^1$H NMR ($CDCl_3$, 250 MHz):2.87 (dt, 4H, H—($C_{ac\ succ}$) $^2J=21$, $^3J=6.6$); 2.58 (t, 4H, H—($C_4$, $C_3$), $^3J=6$); 2.08, 2.01, 1.97 (3 s, 9H, $CH_3$—($C_5$), $CH_3$—($C_7$), $CH_3$—($C_8$)), 1.6–1 (broad multiplet, 24H, $CH_3$—($C_1$)+ 9×$CH_2$, 3×CH tocopherol), 0.88, 0.84 (2 s, 12H, 4×$CH_3$ tocopherol). $^{13}$C NMR ($CDCl_3$, 50 MHz): 177.51, 170.96 (s, $C=O_{acid}$+$C=O_{ester}$); 149.48 (s, $C_{8a}$); 140.44 (s, $C_6$); 126.73 (s, $C_7$); 125.00 (s, $C_5$); 123.10 (s, $C_8$); 117.45 (s, $C_{4a}$); 75.11 (s, $C_2$); 39.42 (t, $C_{1'}$); 37.45 (t, $C_7+C_9+C_3+C_5+C_{11'}$); 32.83 (d, $C_{8'}+C_{4'}+C_{12'}$); 28.97, 28.68, 24.88, 24.50, 21.08, 20.64 ($C_{10'}+C_{66'}+C_2+C_4+CH_{2ac\ succ}$); 28.04 ($CH_3$—($C_2$)); 22.69 ($C_{13'}$); 19.74, 12.7, 12.18, 12.10, 11.99 (CH—($C_{12'}+C_{8'}+C_{4'}$)+$CH_3$—($C_8+C_7+C_5$)+$CH_3$—($C_1$)). IR

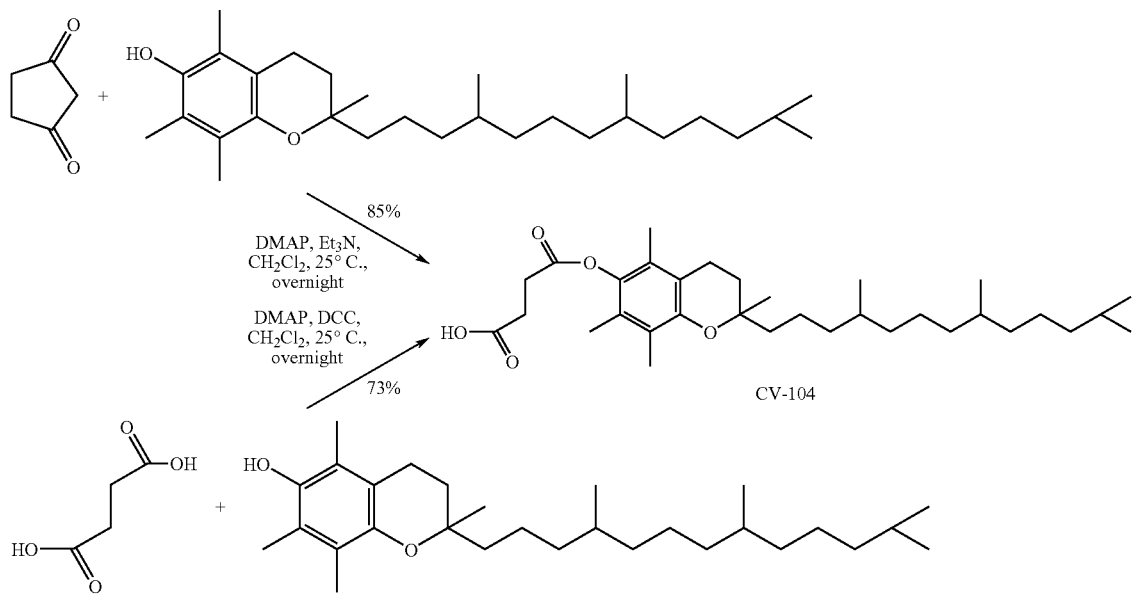

(NaCl): 2924, 2856, 2735, 2638, 2540, 1746, 1694, 1455, 1421, 1378, 1323, 1246, 1155, 1106, 919, 853, 799, 728. MS (CI, $NH_3$): 548 ($[MNH_4]^+$, 100); 531 ($[MH]^+$, 11.3); 530 ($[M]^+$, 3.4). UV ($CH_3CN$): 286 (0.047 at a concentration of 14 µg/ml); 203 (0.61 at a concentration of 14 µg/ml). EA for $C_{33}H_{54}O_5$ (530.78): calc. C, 74.67; H, 10.25; exp. C, 74.85, H, 10.26.

1.2. Tocopheryl Retinyl Succinate (CV-105)

1 eq) dissolved in 5 ml of anhydrous $CH_2Cl_2$ is added. The reaction, performed in the absence of light, is monitored by tlc ($CH_2Cl_2$/PE 2:3): a new, less polar product forms. After reacting overnight, the solvent is filtered and then evaporated off. The product is purified by flash chromatography with EtOAc/PE (2:3) to give a yellow oil (266 mg; 50% yield). A second purification is performed by HPLC (20 g of silica 35, eluent $Et_2O$/PE 1:9).

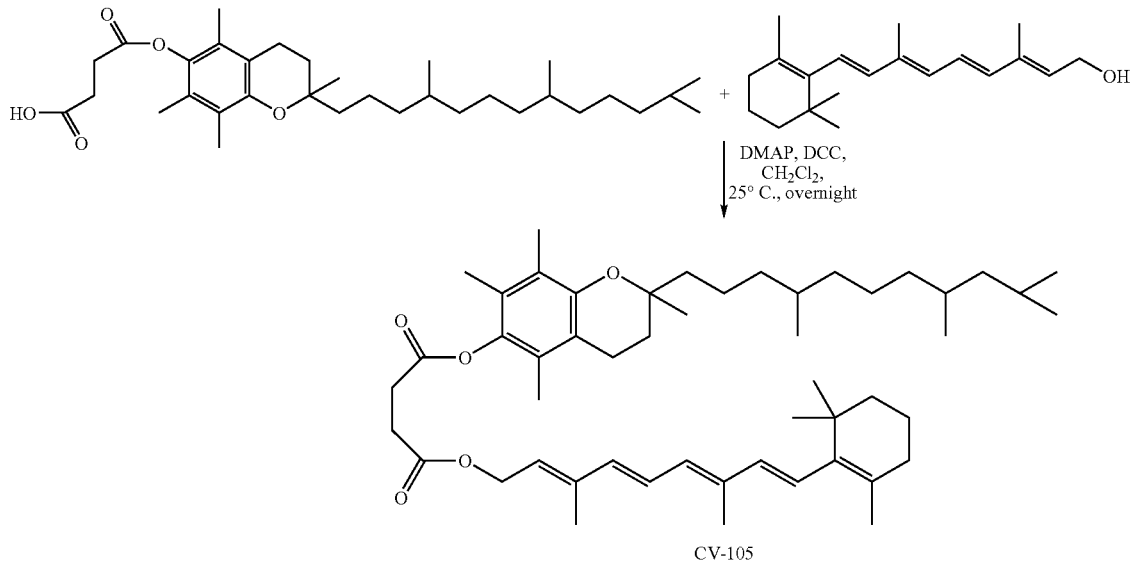

CV-105

CV-104 prepared in example 1.1 (356 mg, 0.67 mmol) is dissolved in 20 ml of anhydrous $CH_2Cl_2$, and DCC (138 mg, 1 eq) and DMAP (20 mg) are directly added thereto. After 10 minutes, a precipitate of dichlorohexylurea (DCU) has already formed, the anhydride of CV-104 having necessarily been formed. After 20 minutes, retinol-vitamin A (192 mg, Starting with 130 mg of the first purified batch, 72 mg of a translucent oil (CV-105) are obtained, i.e. a 28% yield.

EXAMPLE 2

Tocopheryl Cholecalciferyl Succinate(CV-125)

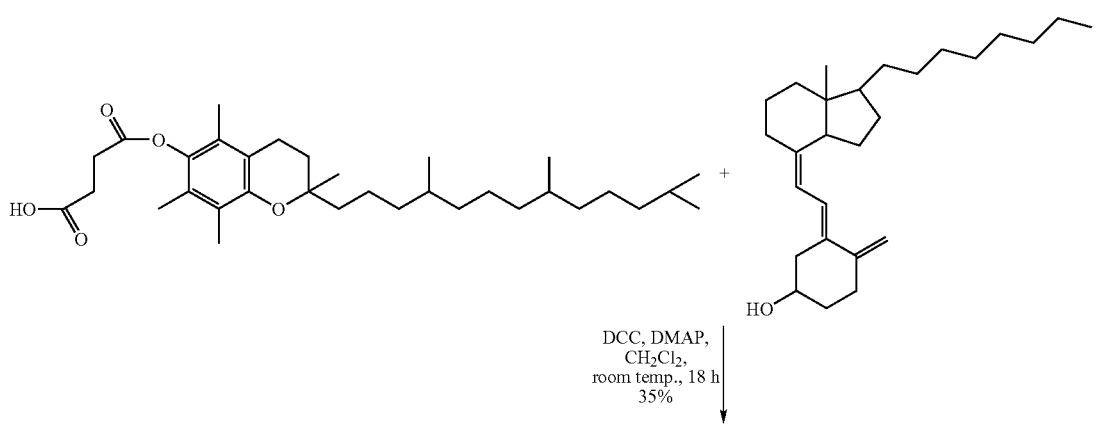

-continued

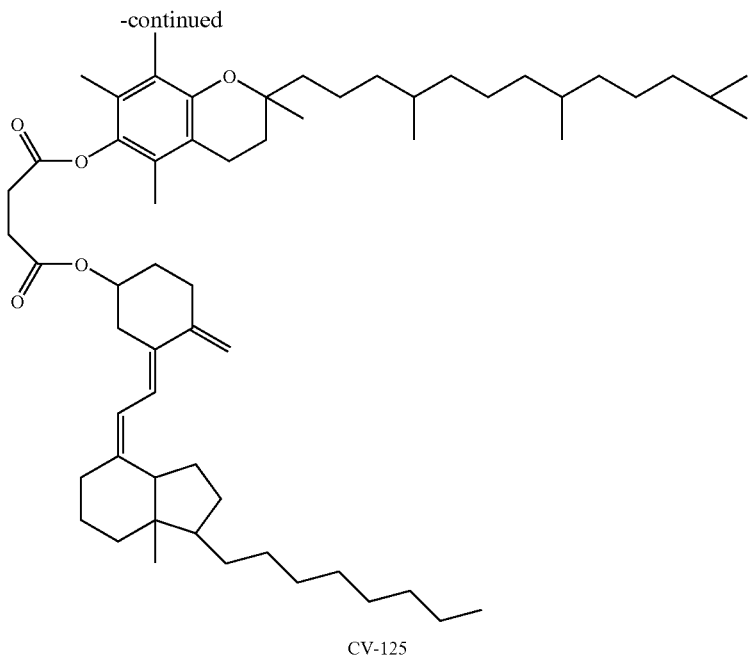

CV-125

CV-104 prepared in example 1.1 (423 mg, 0.798 mmol) is dissolved in 10 ml of anhydrous $CH_2Cl_2$, and DCC (181 mg, 1.1 eq) and DMAP (20 mg) are directly added thereto. After 20 minutes, vitamin $D_3$ (307 mg, 1 eq) dissolved in 10 ml of anhydrous $CH_2Cl_2$ is added. The reaction, performed in the absence of light, is monitored by tlc (EtOAc/PE 2:8 or 5:95): a new, less polar product forms. After reaction overnight, the solvent is filtered and then evaporated off. The product is purified by flash chromatography with EtOAc/PE (5:95) as eluent, 2×12 cm column, 6–8 ml fractions.

Fractions 4 to 10 are evaporated to give 253 mg of tocopheryl calciferyl succinate (CV-125) as a translucent oil (35% yield).

Rf (EtOAc/PE 2:8): 0.91; (EtOAc/PE 5:95): 0.32. $^1H$ NMR ($CDCl_3$, 250 MHz): 6.22 (d, 1H, H—($C_7$), $^3J_{7-8}$=11.2); 6.04 (d, 1H, H—($C_8$), $^3J_{8-7}$=11.2); 5.07 (s, 1H, $CH_2$—($C_4$)); 4.98 (m, 1H, H—($C_1$)); 4.85 (d, 1H, $CH_2$—($C_4$)); 2.92 (dd, 2H, $CH_{2-succ}$, $^2J$=16, $^3J$=6.8); 2.75 (m, 3H, $CH_{2-succ}$+CH—($C_4$), $^2J$=16, $^3J$=6.8); 2.60 (m, 2H, CH—($C_6$)+CH—($C_4$)); 2.4 (m, 2H, CH—($C_6$)+H—($C_{17}$)); 2.09, 2.03, 1.99 (3 s, 9H, $CH_3$—($C_5$), $CH_3$—($C_7$), $CH_3$—($C_8$)), 1.3–0.9 (broad multiplet, 47H, 11×$CH_{2-vitE}$, 3×CH—($C_{12'}$, $C_{4'}$, $C_{8'}$)+11×$CH_{2-vitD3}$); 0.89 and 0.87 (2 s, 21H, 4×$CH_3$—($C_{12'}$, $C_{4'}$, $C_{8'}$)+$C_{25}$); 0.55 (s, 3H, $CH_3$—($C_{13}$)). $^{13}C$ NMR ($CDCl_3$, 50 MHz): 171.72, 171.07 (s, 2×C=$O_{ester}$); 149.47 (s, $C_5$); 144.64 (s, $C_6$); 142.55 (s, $C_{8a}$); 140.50 (s, $C_9$); 134.23 (s, $C_4$); 126.76 (s, $C_7$); 125.00 (s, $C_5$); 123.06 (s, $C_8$); 122.61 (d, $C_7$); 117.53 (d, $C_8$); 117.38 (s, $C_{4a}$); 112.81 (t, $CH_2$—($C_4$)); 75.08 (s, $C_2$); 72.28 (d, $C_1$); 56.66 (d, $C_{17}$); 56.43 (d, $C_{14}$); 45.97 (s, $C_{13}$); 42.19 (t, $C_{12}$); 36.20, 32.84, 32.77 (d, $C_{8'}$+$C_{4'}$+$C_{12'}$); 40.62, 39.57, 39.44, 37.47, 32.23, 31.99, 31.12, 29.50, 29.12, 28.96, 28.08, 27.76 (t,$C_{1'}$+$C_3$+$C_{7'}$+$C_9$+$C_{3'}$+$C_{5'}$+$C_{11}$+$C_{15}$+$C_{10}$+$C_6$+$C_2$+$C_3$+$C_{18-23}$+2×$CH_{2\ ac\ succ}$), 24.89, 24.52, 23.95, 23.64, 22.29, 21.11, 20.67 (t, $C_{10'}$+$C_6$+$C_2$+$C_4$+$C_{24}$+$C_{16}$+$C_{11}$); 22.91, 22.81, 22.71 (q, $CH_3$—($C_2$+2×$C_{13'}$); 19.76, 18.92, 13.05, 12.19, 12.05, 11.89 (q, $CH_3$—($C_8$+$C_4$)+$CH_3$—($C_8$+$C_7$+$C_5$)+$C_{25}$+$CH_3$—($C_2$)). IR (NaCl): 2950, 2867, 2119, 1758, 1736, 1463, 1412, 1377, 1240, 1202, 1146, 1110, 1079, 996, 734. MS (CI, $NH_3$): 914 ([$MNH_4$]$^+$, 100); 897 ([MH]$^+$, 2.86); 896 ([M]$^+$, 2.71). EA for $C_{60}H_{96}O_5$ (896): calc. C, 80.30; H, 10.78; exp. C, 77.36; H, 10.26.

EXAMPLE 3

Tocopheryl Ascorbyl Succinate (CV-106)

3.1. Protected vitamin C (CV-100)

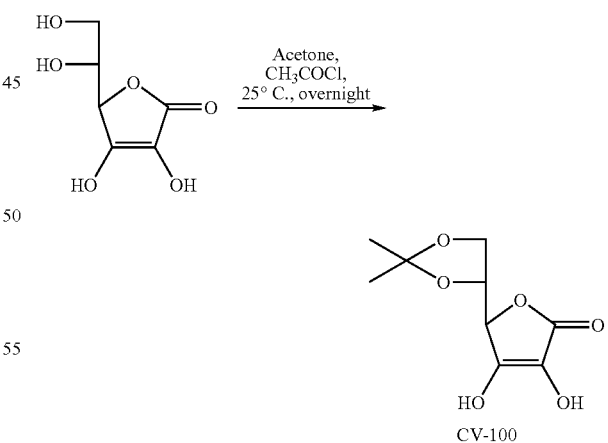

CV-100

250 μl of acetyl chloride are added to a suspension of vitamin C, or ascorbic acid (3 g, 17 mmol) in 30 ml of acetone. The solution becomes clear and a white precipitate then forms. After reaction overnight, the precipitate is filtered off and then rinsed with ice-cold ethyl acetate. The powder obtained is then dried to give 2.96 g (13.7 mmol) of protected vitamin C (CV-100), i.e. an 80.6% yield.

3.2. Tocopheryl Ascorbyl Succinate (CV-106)

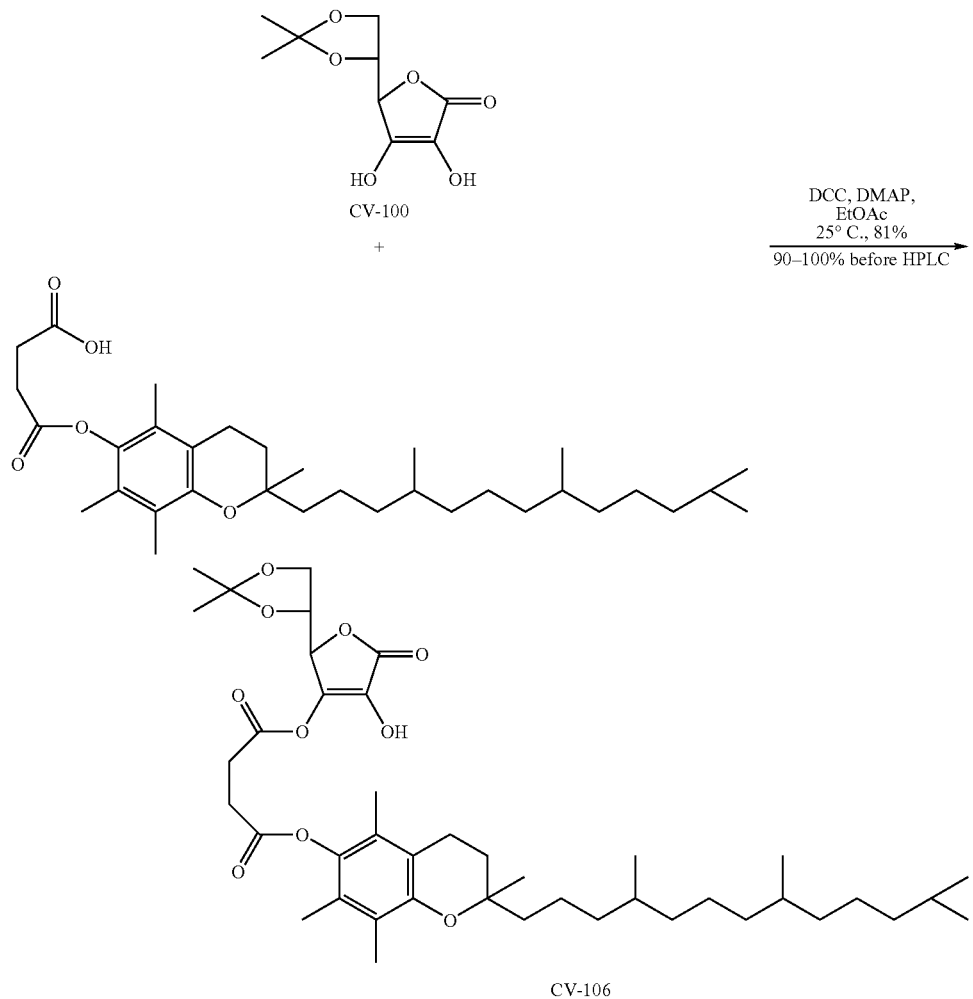

CV-104 prepared in example 1.1 (265 mg, 0.5 mmol) is dissolved in 10 ml of anhydrous EtOAc over about 15 minutes. In parallel, CV-100 prepared in example 3.1 (108 mg, 0.5 mmol, 1 eq) is dissolved in 2 ml of anhydrous tetrahydrofuran (THF) (or 0.2 ml of dimethylformamide, or DMF), followed by 5 ml of anhydrous ethyl acetate, and the solubility is checked after 5–10 minutes. The solution of CV-100 is added to that of CV-104, the solution remains clear, and DMAP (catalytic) and DCC (113 mg, 0.55 mmol, 1.1 eq) are added thereto. The precipitate forms immediately and the reaction is monitored by tlc ($CH_2Cl_2$/EtOAc/MeOH 8:1:1). The reaction is virtually complete after 8 hours.

The mixture is filtered and washed very quickly with 0.1N HCl, and the organic phase is dried over $MgSO_4$ and then evaporated to give CV-106 in the form of a white foam (386 mg).

The coupling appears to take place mainly at C2 rather than at C3 of vitamin C. Specifically, the NMR data are more in accordance with the previously described C2 esters (Cabral J., J. Org. Chem. (1988), 53, 5742–50).

The product is purified by HPLC (30 mg) column of silica 15–25, eluent $CH_2Cl_2$/EtOAc/$NEt_3$ (9:1:0.5%) then $CH_2Cl_2$/EtOAc/$NEt_3$/MeOH (9:1:0.5:2%).

Appearance: white foamy powder

Rf (EtOAc/$CH_2Cl_2$/MeOH 1:8:1): 0.38; (EtOAc/$CH_2Cl_2$/MeOH 1:8:2): 0.48. $^1$H NMR ($CDCl_3$, 250 MHz): 4.66 (d, 1H, $C_4$ $_{vitC}$); 4.39 (ddd, 1H, $C_5$ $_{vitC}$); 4.1 (td, 2H, $C_6$ $_{vitC}$, $^3J_{6-5}$=7.2, $^2J_{6-6'}$=19); 2.92, 2.76 (2t, 4H, H—($C_{ac\ succ}$), $^3J$=6, 6); 2.58 (t, 2H, H—(C4), $^3J$=6); 2.08, 2.0, 1.97 (3 s, 9H, $CH_3$—($C_5$), $CH_3$—($C_7$), $CH_3$—($C_8$)); 1.8–1.7 (m, 2H, H—($C_3$)); 1.7–1.09 (broad multiplet, 23H, 10×$CH_2$, 3×CH tocopherol); 0.87, 0.85 (2 s, 12H, 4×$CH_3$ tocopherol). $^{13}$C NMR ($CDCl_3$, 50 MHz): 171.65, 171.12 (s, 2×C=$O_{ester}$); 159.12 (s, $C_3$ $_{vitC}$); 149.61 (s, $C_6$); 140.46 (s, $C_{8a}$); 126.58 (s, $C_7$); 124.89 (s, $C_5$); 123.16 (s, $C_8$); 117.54 (s, $C_{4a}$); 114.39 (s, $C_2$ $_{vitC}$) 110.57 (s, $C_7$ $_{vitC}$); 75.16 (s, $C_2$); 75.10 (d, $C_4$ $_{vitC}$); 73.68 (d, $C_5$ $_{vitC}$); 65.32 (t, $C_6$ $_{vitC}$); 39.43 (t, $C_1$'); 37.46 (t, $C_3$); 32.84, 32.76, 29.00 (d, $C_{8'}$+$C_{4'}$+$C_{12'}$); 31.09, 29.78, 28.99, 28.90, 28.70, 28.57, 24.88, 24.51, 21.09, 20.65 (t, $C_7$+$C_9$+$C_{3'}$+$C_{5'}$+$C_{11'}$+$C_{10'}$+$C_{6'}$+$C_{2'}$+$C_{4'}$+2×$CH_2$ $_{ac\ succ}$); 25.86, 25.61 (q, $C_{8\ and\ 8'\ vitC}$); 21.09, 20.65 (q, $CH_3$—($C_2$)+2×$C_{13'}$); 22.81, 22.72, 13.00, 12.15, 11.89 (q, $CH_3$—($C_8$+$C_{4'}$)+$CH_3$—($C_8$+$C_7$+$C_5$)). IR (NaCl): 3248, 2929, 2856, 1756, 1670, 1605, 1453, 1409, 1374, 1322, 1256, 1213, 1141, 1066, 885, 852, 820, 736, 700. MS (CI, $NH_3$): 746 ($[MNH_4]^+$, 96); 728 ($[M]^+$, 2.6); 612 (6.7); 548 $[MNH_4]^+$ of CV-104 (20.3); 423 (16); 234 $[MNH_4]^+$ of CV-100 (59). EA for $C_{42}H_{64}O_{10}$ (728): calc. C, 69.20; H, 8.85; exp. C, 67.17; H, 8.83.

EXAMPLE 4

Enzymatic hydrolysis 4.1. Procedure

150 µl of a 1 mM solution in dimethyl sulphoxide (DMSO) are placed in a dish containing an HaCaT keratinocyte line (75 cm²) in 15 ml of serum alone. The cells are placed in the incubator at 37° C. for 24 hours. The medium is extracted with 15 ml of ethyl acetate. The organic phase is then isolated and evaporated off.

The cells are extracted by sonication into 2×15 ml of an ice-cold mixture consisting of chloroform and methanol (1:2.5). After centrifugation, the organic phase collected is evaporated to dryness. For each test, a control is performed on a dish containing cells and a substrate-free medium to take account of a possible chemical degradation of the substrate.

The presence of esterase activity in the human keratinocytes is checked by means of a substrate, 4-methylumbelliferyl palmitate. The precursor according to the invention, used as pseudosubstrate, is the tocopheryl retinyl succinate prepared according to example 1.

4.2. Results

The results are collated in the following table:

| Substrate | Degree of hydrolysis in 24 hours of incubation | Released part |
|---|---|---|
| 4-Methylumbelliferyl palmitate | 2.7% ± 2% | 4-methylumbeliferone |
| Tocopheryl retinyl succinate | 5% ± 3% | vitamins A and E |

The values obtained show a simultaneous release of vitamins E and A from the tocopheryl retinyl succinate. These results confirm the very good cleavage kinetics in the case of succinate esters via the keratinocyte esterases. Furthermore, a release with a reservoir effect is observed, since the undegraded precursor is found in the sample taken.

The invention claimed is:

1. A bioprecursor of formula (I)

(I)

in which
$A_1$ represents a tocophenyl radical and A2 represents a retinyl radical, a cholecalciferyl radical, or an ascorbyl radical;
X and Y represent, independently of each other, a hydrogen atom, a hydroxyl group or a ($C_1$–$C_{20}$)alkyl group; and
n represents an integer between 0 and 10.

2. The bioprecursor as claimed in claim 1, characterized in that it is chosen from the group consisting of tocopheryl retinyl succinate, tocopheryl cholecalciferyl succinate and tocopheryl ascorbyl succinate.

3. The bioprecursor as claimed in claim 1, characterized in that it is chosen from

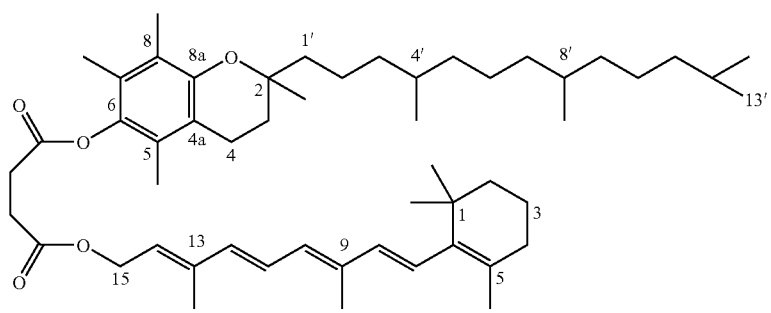

-continued

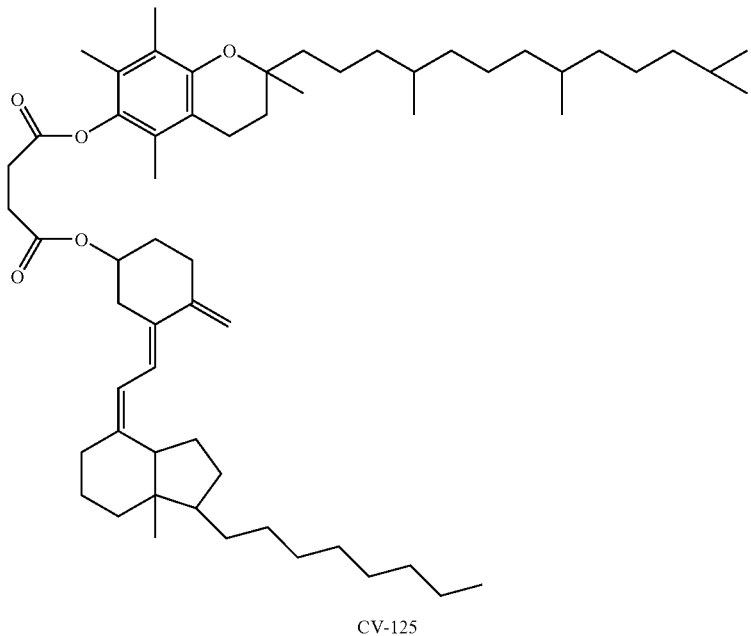

CV-125

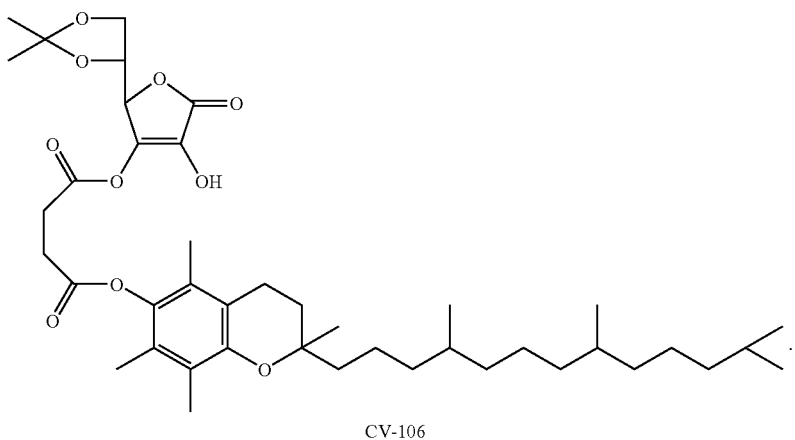

CV-106

4. A pharmaceutical composition, characterized in that it contains at least one bioprecursor as claimed in claim 1 combined with a vehicle that is suitable for percutaneous administration.

5. The pharmaceutical composition as claimed in claim 4, characterized in that it contains from 0.001% to 10% by weight and preferably 0.01% to 0.1% by weight of bioprecursors relative to the total weight of the composition.

6. The pharmaceutical composition as claimed in claim 4, characterized in that it is in the form of an oil-in-water (O/W) or water-in-oil (W/O) emulsion.

7. The pharmaceutical composition as claimed in claim 4, characterized in that it is in the form of spherules.

8. The pharmaceutical composition claimed in claim 6, characterized in that the proportion of the fatty phase ranges from 5% to 60% by weight and preferably from 5% to 56% by weight relative to the total weight of the composition.

9. The pharmaceutical composition as claimed in claim 4, characterized in that it also contains acceptable cosmetic or dermatological additives.

10. A process for preparing the bioprecursors as claimed in claim 1, characterized in that a compound of formula (II)

$$A_1\text{-H} \quad (11)$$

in which $A_1$ is as defined in claim 1, is reacted with a compound of formula (III)

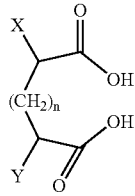

(III)

in which X and Y are as defined in claim 1, in a mixture containing a solvent, for instance anhydrous dichloromethane, triethylamine, II, III, dicyclohexylcarbodiimide (DCC) and dimethylaminopyridine (DMAP), to give a compound of formula (IV)

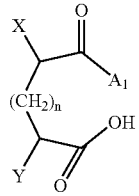

(IV)

which compound is reacted under the same conditions as above with a compound of formula (V)

$$A_2\text{-H} \quad (V)$$

to give the compound of formula (I).

* * * * *

UNITED STATES PATENT AND TRADEMARK OFFICE
CERTIFICATE OF CORRECTION

PATENT NO. : 7,084,172 B2  Page 1 of 1
APPLICATION NO. : 10/489736
DATED : August 1, 2006
INVENTOR(S) : Redoules et al.

It is certified that error appears in the above-identified patent and that said Letters Patent is hereby corrected as shown below:

Column 16, line 59, change "from 5% to 60% by weight and preferably from 5% to 56%" to read -- from 5% to 80% by weight and preferably from 5% to 50%--

Signed and Sealed this

Fifth Day of December, 2006

JON W. DUDAS
*Director of the United States Patent and Trademark Office*